US00PP10299P

United States Patent [19]

Tristram

[11] Patent Number: Plant 10,299

[45] Date of Patent: Mar. 24, 1998

[54] COREOPSIS PLANT NAMED 'WALCOREOP'

[76] Inventor: David Ralph Tristram, Walberton Nursey, Yapton Lane, Walberton, Arundel, West Sussex., England, BN18 0AS

[21] Appl. No.: 761,759

[22] Filed: Dec. 5, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A distinct cultivar of Coreopsis plant named 'Walcoreop', characterized by its uniform, spreading and compact growth habit; moderate to rapid growth rate; moderate to high vigor; large inflorescences that are saucer-shaped; numerous inflorescences that flower continuously throughout the flowering season; bright yellow ray and disc florets; long, narrow ray florets; long, narrow bracts; and good garden performance.

1 Drawing Sheet

The present invention relates to a new and distinct cultivar of garden Coreopsis plant, botanically known as *Coreopsis grandiflora* and referred to by the cultivar name Walcoreop and known by the trade name Flying Saucers.

The new cultivar is a product of a planned breeding program conducted by the inventor in Walburton, Arundel Sussex, United Kingdom. The objective of the breeding program as to create new garden Coreposis cultivars having uniform plant habit, good vigor, large inflorescences and abundant flowers throughout the flowering season.

The new cultivar originated from a series of self-pollinated crosses made by the inventor of plants of the species *Coreopsis grandiflora* starting in 1980. Seed derived from the best progeny were sown in 1991 and the new Coreopsis was selected from the best of these seedlings in 1992 in a controlled environment in Walburton, Arundel, Sussex, United Kingdom.

Asexual reproduction of the new cultivar by terminal cuttings taken at Walburton, Arundel, Sussex, United Kingdom, has shown that the unique features of this new Coreopsis are stable and reproduced true to type in successive generations.

The following traits have been repeatedly observed and are determined to be unique characteristics of 'Walcoreop'. These characteristics in combination distinguish 'Walcoreop' as a new and distinct cultivar:

1. Uniform, speading and compact growth habit.
2. Moderate to rapid growth rate and moderate to high vigor.
3. Large inflorescences that are slightly cupped upwards or saucer-shaped.
4. Numerous inflorescences that flower continuously throughout the flowering season.
5. Bright yellow ray and disc florets.
6. Long, narrow ray florets.
7. Long, narrow bracts.
8. Good garden performance.

The cultivar Walcoreop has not been observed under all possible environmental conditions. The phenotype may vary somewhat with variations in environment such as temperature, daylength and light intensity, without, however, any variance in genotype.

Plants of the new Coreopsis can be compared to plants of the nonpatented cultivar Badengold. However, in side-by-side comparisons conducted in Walburton, Arundel, Sussex, United Kingdom, under outdoor summer conditions, plants of the new Coreopsis differed from plants of the cultivar Badengold in the following characteristics:

1. Plants of the new Coreopsis are more compact, denser and more spreading than plants of the cultivar Badengold.
2. Plants of the new Coreopsis are more freely branching than plants of the cultivar Badengold.
3. Stems of plants of the new Coreopsis are glabrous or have minute hairs whereas stems of plants of the cultivar Badengold are pubescent with hairs 1 to 2 mm in length.
4. Leaves of plants of the new Coreopsis are narrower than plants of the cultivar Badengold.
5. Plants of the new Coreopsis flower from June through October whereas plants of the cultivar Badengold only flower until about August in the Northern Hemisphere.
6. Ray florets of plants of the new Coreopsis are slightly longer and narrower than ray florets of plants of the cultivar Badengold.
7. Plants of the new Coreopsis have shorter peduncles than plants of the cultivar Badengold.
8. Bracts of plants of the new Coreopsis are twice as long as bracts of plants of the cultivar Badengold.

Plants of the new Coreopsis can also be compared to plants of the nonpatented cultivar Pot of Gold. However, in side-by-side comparisons conducted in Walburton, Arundel, Sussex, United Kingdom, under outdoor summer conditions, plants of the new Coreopsis differed from plants of the cultivar Pot of Gold in the following characteristics:

1. Plants of the new Coreopsis are usually shorter and more spreading than plants of the cultivar Pot of Gold.
2. Plants of the new Coreopsis are more freely branching than plants of the cultivar Pot of Gold.
3. Stems of plants of the new Coreopsis are glabrous or have minute hairs whereas stems of plants of the cultivar Pot of Gold are pubescent with hairs about 1 mm in length.
4. Plants of the new Coreopsis flower from June through October whereas plants of the cultivar Pot of Gold only flower until about August in the Northern Hemisphere.
5. Ray florets of plants of the new Coreopsis are slightly longer and narrower than ray florets of plants of the cultivar Pot of Gold.
6. Plants of the new Coreopsis have shorter, but stronger peduncles than plants of the cultivar Pot of Gold.
7. Bracts of plants of the new Coreopsis are twice as long as bracts of plants of the cultivar Pot of Gold.

A detailed comparison of plants of the new Coreopsis and the cultivars Badengold and Pot of Gold appears in Chart A at the end of the specification.

The accompanying colored photograph illustrates the overall appearance of the new cultivar, showing the colors as true as it is reasonably possible to obtain in colored reproductions of this type. The photograph comprises a top perspective view of typical flowering plants of 'Walcoreop' in a garden setting. Foliage and floret colors in the photograph may appear different from the actual colors due to light reflectance.

In the following description, color references are made to The Royal Horticultural Society Colour Chart except where general terms of ordinary dictionary significance are used. The following observations and measurements describe plants grown outdoors during the summer in Walburton, Arundel, Sussex, United Kingdon. Measurements and numerical values represent ranges are averages for six typical flowering plants.

Botanical classification: *Coreopsis grandiflora* cultivar Walcoreop.

Commercial classification: Garden Coreopsis, trade name: Flying Saucers.

Parentage: Progeny selection of self-pollinated plants of the species *Coreopsis grandiflora*.

Propagation:

*Type.*—Terminal tip cuttings.

*Time to rooting.*—Summer: About 14 days at 21C. Winter: About 21 days at 16C.

*Rooting habit.*—Fine, fibrous and somewhat branched.

Plant description:

*Appearance.*—Perennial herbaceous garden plant. Uniform, rounded, spreading, and relatively compact. Freely branching.

*Growth rate.*—Moderate to rapid.

*Vigor.*—Moderate to high.

*Plant height.*—About 46 cm.

*Foliage description.*—Leaves opposite with 1 to 5 leaflets, oddly pinnate. Leaf shape: Linear, oblanceolate. Leaf size, fully expanded: Length: About 15 to 23 cm. Width: About 1.3 to 2.5 cm. Leaf apex: Obtuse. Leaf base: Attenuate. Leaf margin: Entire. Leaf texture: Abaxial surface smooth, adaxial surface slightly satiny Venation: Abaxial surface: Recessed mid-vein, lateral veins scarcely visible. Adaxial surface: Prominent mid-vein. Petiole length: Up to 5 cm. Color: Young foliage abaxial surface: 146A. Young foliage adaxial surface: 147C. Fully expanded foliage abaxial surface: 146A. Fully expanded foliage adaxial surface: 147C. Petiole: 146D.

Inflorescence description:

*Appearance.*—Daisy-type inflorescence form. Inflorescences borne on terminals above foliage, arising from leaf axils. Disc and ray florets arranged acropetally on a flat capitulum. One inflorescence per flowering stem. Inflorescences are slightly cupped upwards and appear saucer-shaped. Inflorescences last about one week on the plant. Disc florets persistent and ray florets self-cleaning.

*Flowering response.*—Under natural conditions, plants flower continuously from June to October in the Northern Hemisphere.

*Inflorescence size.*—Diameter: About 7.5 cm. Depth (height): About 1.3 cm. Diameter of disc: About 1 to 1.6 cm.

*Opening inflorescences.*—Bud shape: Spherical, globular. Bud size: Length: About 1 to 1.3 cm. Width: About 1 to 1.3 cm. Bud color: 199A/197A/148A.

*Ray florets.*—Shape: Obovate. Size: Length: About 3.2 to 4.1 cm. Width: About 1.9 to 2.5 cm. Apex: Dentate, generally with four uneven coarse teeth. Margin: Entire. Texture: Dull, satiny. Number of ray florets per inflorescence: Usually 7 to 15. Color: When opening: 13B. Mature, abaxial surface: 14B. Mature, adaxial surface: 13B. With development darkening to: 21A.

*Disc florets.*—Shape: Narrow, funnel-shaped. Size: Length: About 6 to 10 mm. Width: About 1 mm. Number of disc florets per inflorescence: About 50 to 150. Color: Immature: 21A. Mature: 21A/200D.

*Peduncle.*—Aspect: Strong and erect. Length: About 15 to 30.5 cm. Texture: Glabrous, smooth. Color: 146D.

*Sepals.*—Shape: Triangular. Size: Length: About 9 to 15 mm. Width: About 5 to 9 mm. Calyx size: Length: About 6 mm. Diameter: About 1.3 to 1.9 cm. Apex: Acute. Margin: Entire. Texture: Smooth. Number of sepals per inflorescence: Usually 8 to 10. Color: Mature, abaxial surface: 146C/199B. Mature, adaxial surface: 146C/199B.

*Bracts.*—A whorl of 8 to 10 bracts below the sepals are held horizontally or slightly cupped upwards or saucer-shaped. Usually 4 times as long as wide.

*Reproductive organs.*—Androecium: Anther size: About 2 mm. Anther color: 200D. Pollen: Moderate, 15A in color. Gynoecium: Stigma color: 16C. Style length: About 6 to 9 mm. Style color: 11C.

Disease resistance: No known Coreopsis diseases observed to date on plants grown under commercial greenhouse conditions.

Seed production: Seed production has not been observed as plants are nearly sterile.

CHART A

| CHARACTERISTIC | 'WALCOREOP' | 'BADENGOLD' | 'POT OF GOLD' |
|---|---|---|---|
| PLANT SHAPE | Bushy, spreading | Bushy, upright | Bushy |
| GROWTH HABIT | Compact | Open | Compact |
| PLANT HEIGHT | About 46 cm | About 61 to 91 cm | About 46 to 76 cm |
| BRANCHING HABIT | Freely | Low to moderate | Moderate |
| STEM TEXTURE | Glabrous or with minute hairs | Pubescent, hairs 1 to 2 mm in length | Pubescent, hairs 1 mm in length |
| LEAF WIDTH | 1.3 to 2.5 cm | 2.5 to 5.1 cm | 1.3 to 2.5 cm |
| YOUNG LEAF COLOR, ABAXIAL SURFACE | 146A | 147A/147B | 147A/147B |
| YOUNG LEAF COLOR, ADAXIAL SURFACE | 147C | 147C | 147C |
| MATURE LEAF COLOR, ABAXIAL SURFACE | 146A | 147A/147B | 147A/147B |
| MATURE LEAF COLOR, ADAXIAL SURFACE | 147C | 147C | 147C |

CHART A-continued

| CHARACTER-ISTIC | 'WALCOREOP' | 'BADENGOLD' | 'POT OF GOLD' |
|---|---|---|---|
| TIME OF FLOWERING | July through October | July through August | July through August |
| RAY FLORET LENGTH | 3.2 to 4.1 cm | 2.9 to 3.8 cm | 2.9 to 3.8 cm |
| RAY FLORET WIDTH | 1.9 to 2.5 cm | 2.2 to 3.2 cm | 2.2 to 2.9 cm |
| NUMBER OF RAY FLORETS PER INFLOR-ESCENCE | 7 to 15 | 7 to 11 | 7 to 15 |
| DIAMETER OF DISC | 1 to 1.6 cm | 1.3 to 1.9 cm | 1 to 1.6 cm |

CHART A-continued

| CHARACTER-ISTIC | 'WALCOREOP' | 'BADENGOLD' | 'POT OF GOLD' |
|---|---|---|---|
| PEDUNCLE LENGTH | 15 to 30.5 cm | 30.5 to 61 cm | 23 to 38 cm |
| PEDUNCLE STRENGTH | Strong | Strong | Moderate |
| BRACT SIZE | 4x as long as wide | 2x as long as wide | 2x as long as wide |

It is claimed:

1. A new and distinct cultivar of Coreopsis plant named 'Walcoreop', as illustrated and described.

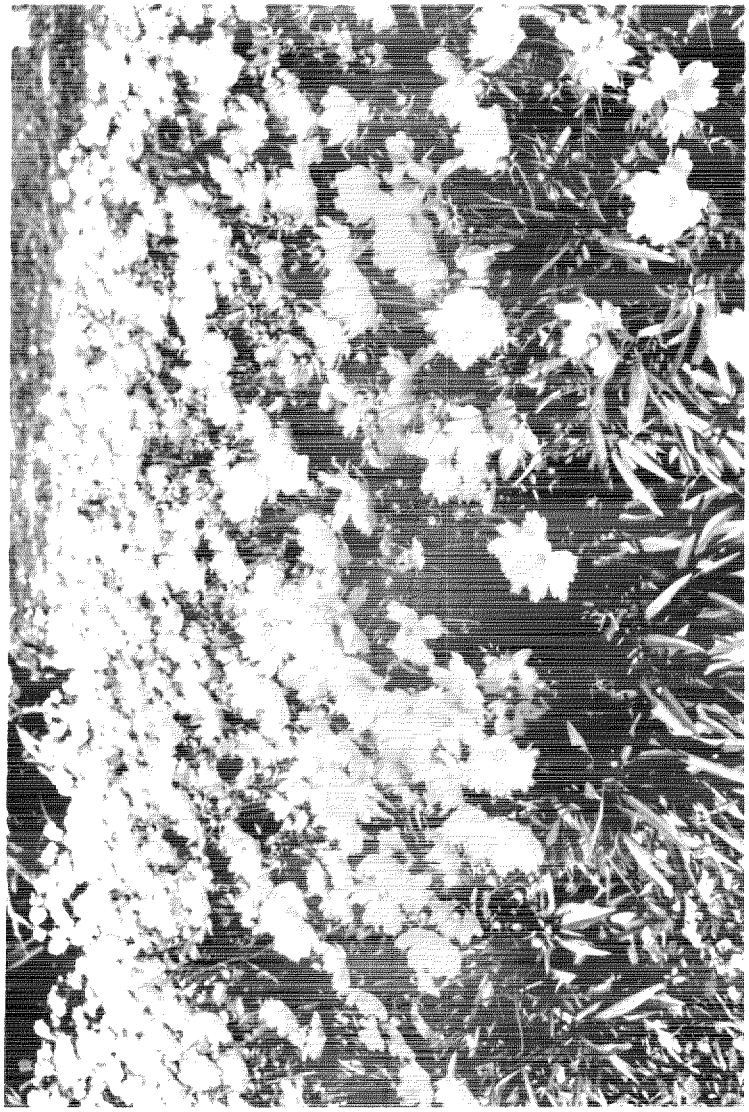

* * * * *